(12) United States Patent
Gavaris et al.

(10) Patent No.: US 11,971,353 B2
(45) Date of Patent: Apr. 30, 2024

(54) MULTIPLEXED SURFACE PLASMON RESONANCE SENSING OF ANALYTES IN LIQUID SAMPLE

(71) Applicant: LacriSciences, LLC, Washington, DC (US)

(72) Inventors: Paul T. Gavaris, Potomac, MD (US); Chris D. Geddes, Bel-Air, MD (US); Ali Ghovanlou, Potomac, MD (US)

(73) Assignee: LACRISCIENCES, LLC, Washington, DC (US)

( * ) Notice: Subject to any disclaimer, the term of this patent is extended or adjusted under 35 U.S.C. 154(b) by 0 days.

(21) Appl. No.: 17/070,489

(22) Filed: Oct. 14, 2020

(65) Prior Publication Data
US 2021/0109020 A1   Apr. 15, 2021

Related U.S. Application Data

(60) Provisional application No. 62/915,301, filed on Oct. 15, 2019.

(51) Int. Cl.
*G01N 21/552* (2014.01)
*G01N 33/543* (2006.01)

(52) U.S. Cl.
CPC ..... *G01N 21/554* (2013.01); *G01N 33/54373* (2013.01)

(58) Field of Classification Search
CPC ........... G01N 21/554; G01N 33/54373; G01N 2201/0221; G01N 21/553

(Continued)

(56) References Cited

U.S. PATENT DOCUMENTS 8,094,316 B1   1/2012   Homola et al.
8,249,682 B2   8/2012   Cappo et al.
(Continued)

FOREIGN PATENT DOCUMENTS

JP   2003042947   2/2003
JP   2012233860   11/2012
WO   200109388    2/2001

OTHER PUBLICATIONS

Homola, J. et al. Mutli-Analyte Surface Plasmon Resonance Biosensing, www.elsevier.com/locate/ymeth, Methods 37, 2005, pp. 26-36, Institute of Radio Engineering and Electronics, Academy of Sciences of the 18251 Prague, Czech Republic.

(Continued)

*Primary Examiner* — Matthew D Krcha
*Assistant Examiner* — Jacqueline Brazin
(74) *Attorney, Agent, or Firm* — R. Neil Sudol; Henry D. Coleman

(57) ABSTRACT

A hand-held or portable SPR device focuses light at two or more positions on a noble metal sensor surface, functionalized to enable detection of different SPR curves and their respective minima. The detection is accomplished substantially simultaneously by obtaining SPR signals contemporaneously from the different locations on the sensor surface, on the same sensor. The SPR device may incorporate multiple light sources or a single light source with a beam that is shifted by deflectors in seriatim to focus on different positions on along the functionalized sensor surface. To control wettability of the sensor surface (to augment multiplexing), the sensor surface may include i) the addition of surface assembled monolayers (SAMs) and ii) surface bombardment by gaseous plasmas, most notably $O_2$.

20 Claims, 4 Drawing Sheets

(58) Field of Classification Search
USPC .............................................................. 435/5
See application file for complete search history.

(56) References Cited

U.S. PATENT DOCUMENTS

| | | | |
|---|---|---|---|
| 2007/0211254 A1* | 9/2007 | Matsushita ........ | G01N 21/7703 |
| | | | 356/445 |
| 2009/0005660 A1* | 1/2009 | Cappo .................... | G01N 33/84 |
| | | | 600/318 |
| 2018/0003706 A1 | 4/2018 | Trenholm et al. | |

OTHER PUBLICATIONS

Dias A.D. et al, Recent Advances in Bioprinting and Applications for Biosensing, Biosensors 2014, 4, 111-136; Department of Biomedical Engineering, Rensselaer Polytechnic Institute, 110 Eighth St., Troy, NY.

* cited by examiner

MULTIPLEXED SURFACE PLASMON RESONANCE SENSING OF ANALYTES IN LIQUID SAMPLE

FIELD OF THE INVENTION

This invention relates to devices and methods using surface plasmon resonance to detect or identify components dissolved or suspended in liquid and to measure concentrations of such components. The target constituents include viruses, bacteria, endosomes, enzymes, cations, anions, lipids, pharmaceuticals, drugs, and small molecules. The invention can be used in analyzing and measuring human or animal tears. Additionally, the invention can identify and measure concentrations of solutes in other body fluids, or can be utilized similarly to detect pathogens in foods or environment.

BACKGROUND OF THE INVENTION

U.S. Pat. No. 8,249,682 discloses an apparatus that uses Surface Plasmon. Resonance (SPR) technology as a sensing platform to detect analytes or chemical markers, particularly including antigens, in a liquid sample such as a human or animal tear. Specific antibodies are immobilized on or adhered to an SPR sensor surface, which leads to a signal generation, specific to respective chemical markers such as antigens.

Portable SPR devices pursuant to the teachings of U.S. Pat. No. 8,249,682 are one-dimensional SPR devices. In other words the entire gold-plated surface area of the disposable sensor prism is functionalized only for detection of one analyte in a tear sample, or is not functionalized at all, as when the device uses only a noble metal film to measure the osmolarity of tears.

The immobilization of antibodies on an SPR sensing surface enables detection of unknown concentrations of antigenic analytes in a tear sample, thereby facilitating diagnosis of eye diseases and conditions. The same procedure can be used to detect solutes or analytes in any liquid, for medical or other purposes.

The computer analysis of the patterns of light absorption determines, for instance, absorption-line positions or angles of maximum absorption by the sensing surface. Thus, the operating of the surface plasmon resonance apparatus may more specifically include operating the computer or microprocessor to determine a surface resonance angle or absorption-line position from each of the electrical signals.

The apparatus of U.S. Pat. No. 8,249,682 contemplates that different analytes or solutes in a liquid sample migrate at different rates to the sensing surface. Different SPR minima are detected then in a sequence to provide information on multiple constituents of a liquid sample. A problem arises when the migration rates are not sufficiently different to facilitate detection of respective SPR minima. Also there exists a need to reduce testing time and materials.

OBJECTS OF THE INVENTION

It is an object of the present invention to provide an improved device and/or a novel and improved methodology utilizing SPR for facilitating effectively simultaneous detection of the presence of multiple solutes or analytes in a liquid sample.

It is an associated particular object of the invention to provide an improved second-generation SPR device utilizing improved methodology to measure the concentrations of at least two components of a liquid sample simultaneously via a single sensor.

It is further an object of the invention to provide such a device that can be used clinically, or in testing food samples at any point along a production chain or at any point along a trade channel, including in the home.

Yet another object of the present invention, is to provide such a device and/or method that is simple to use, cost effective, safe and sanitary.

These and other objects of the present invention will be apparent from the drawings and description herein. Although every object of the invention is believed to be attained in at least one embodiment of the invention, there is not necessarily any single embodiment that achieves all of the objects of the invention.

SUMMARY OF THE INVENTION

The present invention uses novel technology to produce a new hand-held or portable SPR device like that described in U.S. Pat. No. 8,249,682, the disclosure of which is hereby incorporated by reference. Pursuant to the invention, a multi-dimensional or multiplexed detection and measuring device exhibits differentially functionalized locations or regions on a gold-plated sensor surface that create a number of detection channels for simultaneous detection of dissolved or suspended components in a liquid sample, such as in human tear. The invention represents a sea change in the state of the art of using SPR to detect and quantify dissolved constituents of, and analytes in, liquid samples exemplarily including body fluids and food samples. In the field of medicine, the invention provides for real-time point-of-care diagnostics, a long-awaited goal of the industry.

Thus, the present invention contemplates focusing light at two or more positions on a noble metal sensor film or coating particularly on an undersurface thereof, from which different SPR curves (with their respective analyte-identifying minima) can be observed for the respective positions. By generating one or more SPR curves from different positions on the sensor surface, one can analytically determine concentrations of one or more analytes in a single liquid sample placed on the sensor surface. Pursuant to the present invention, a hand-held or portable SPR measurement device can detect the presence, and measure the concentrations, of one or more constituent analytes in a liquid sample that selectively adhere to the sensor surface at respective locations along or on that surface, where the sensor surface is provided on a single disposable sensor prism removably attachable to the SPR measurement device. The signals from the different sensor locations, elicited upon directing each light source to strike the sensor film or coating at the different positions, may be collected substantially simultaneously in real time by multiplexing (creating) SPR signals from the different locations on the sensor surface and directing them onto a photodetector device exemplarily an array of opto-electrical transducers such as a charge-coupled device.

An essential enabling technology for precise deposition (both location as well as the microscopic layer thickness) of adhesion linking layer, the immobilization matrix, and the ligand necessary for functionalization of the SPR surface is the Jetting-based bioprinting technology. Jetting-based bioprinting is a non-contact technique where 2D structures are generated using picolitre bio-ink droplets layered onto a substrate. The jetting-based bioprinting methods can eject droplets of picolitre volume with high spatial resolution.

Pursuant to the present invention, an SPR device as described in U.S. Pat. No. 8,249,682 may incorporate multiple light sources or a single light source with a beam that is directed to focus on different positions on or along the sensor by optical, mechanical and/or electronic means. (For instance, electrical signals from a microprocessor may operate electromechanical servomechanisms or piezoelectric actuators to mechanically adjust optical focusing elements.) To enable differential functionalization of the sensor surface (which enables multiplexing) and optionally, in some cases, to control or modify wettability of the sensor surface, the present invention contemplates the addition of surface assembled monolayers (SAMs). Different SAMs may be used to couple respective solute- or analyte-binding agents to the noble metal sensor surface, where the binding agents may include antibodies preselected for attracting and holding respective solutes or analytes, namely, antigens, in a liquid sample.

A multiplexed analyte-sensing apparatus using surface plasmon resonance (SPR) comprises, in accordance with the present invention, a sensing surface for contacting a liquid sample and configured to interact with a plurality of different solutes or analytes in the liquid sample, a light-sensing device, and a computer or microprocessor operatively linked to the light-sensing device for receiving therefrom a plurality of electrical signals encoding patterns of light absorption by the sensing surface. The computer or microprocessor is programmed to analyze data from the light-sensing device to determine concentrations of the plurality of different solutes in a single contiguous or unitary sample in contact with the sensing surface by analyzing the patterns. The sensing surface is provided with a plurality of different molecular elements or ligands configured to bind with respective ones of the plurality of different solutes, the different molecular elements or ligands being disposed on the sensing surface at respective predetermined regions spaced from each other. Thus, the sensing surface is spatially coded or functionally divided (patterned) for detecting the presence of respective solutes or analytes and their concentrations. The SPR apparatus further comprises at least one light source and optical transmission elements disposed at least in part between the light source and the sensing surface and configured for directing respective beams of electromagnetic radiation toward respective ones of the predetermined regions and on an underside of the sensing surface, opposite the liquid sample, so that reflected beams from the underside of the sensing surface impinge on the light sensing device. (Typically the underside of the noble metal substrate or film is attached via a chromium layer to the prism of the sensor body.) The optical transmission elements may be disposed in part also between the solute sensing surface and the light sensing device.

Pursuant to further features of the present invention, (a) the solute sensing surface is provided with at least one noble metal film, layer or coating, the predetermined regions being on the at least one metal film, layer or coating, and (b) at least one surface-assembled monolayer is provided on the sensing surface to control or adjust the wettability of the sensing surface, that is, to control the degree of spreading of the liquid sample over the sensing surface. Wettability may be enhanced, for instance, by deposition of a surface-assembled monolayer so that the liquid sample moves into effective contact with the at least one metal film, layer or coating at one or more of the predetermined regions. The surface-assembled monolayer may include alkane thiol groups attached to the at least one metal film, layer or coating. The alkane thiol groups can additionally function to attach the different solute-binding molecular elements or ligands to the metal film, layer, or coating.

At least some of the alkane thiol groups may be each provided with a terminal hydrophobic head taken from the group consisting of acidic hydrophobic heads, hydroxyl hydrophobic heads, or amino groups. The terminal hydrophobic head may be $SH-(CH_2)_n-COOH$ or $SH-(CH_2)_n$.

The surface-assembled monolayer (SAM) may include both hydrophilic and hydrophobic elements in preselected amounts to vary the hydrophilicity/hydrophobicity of the surface-assembled monolayer over the predetermined regions. This differential disposition of SAMs on the sensing surface is effectuated by use of a printing device applying pico- or nano-sized droplets of SAM components.

Preferably, the SPR apparatus additionally comprises a hand-holdable housing or casing. The sensing surface is disposed on the housing or casing. The one or more light sources, the light-sensing device, the computer or microprocessor and the optical transmission elements are contained inside the housing or casing.

The computer or microprocessor is configured to detect multiple SPR signals from analytes in the liquid sample effectively simultaneously. An electrical signal from the light sensing device includes signals of different optoelectrical elements or pixels in a predetermined sequence whereby the computer or microprocessor monitors SPR light signals from different regions of the sensor surface substantially in real time and in interleaved simultaneity. The real-time point-of-care diagnostics provided by the invention entails multiple analyses with one test and on same 1×3 mm sensor surface to enhance efficiency of medical professionals, enabling earlier initiation of treatment and at significantly reduced medical costs.

The liquid sample exemplarily consists of biological fluid, human fluid, animal fluid, food, or beverages. The solutes or analytes, the presence and/or concentrations of which are detected, may be cells, bacteria, insect constituents, vegetable constituents, viruses exemplarily from tissue or respiratory fluids either directly or their respective lysates, proteins, DNA and RNA, dissolved cations or anions, endosomes, enzymes, lipids, pharmaceutical compounds, natural and artificial drugs, small molecules, or dissolved gasses. The enzymes may include mmp-9; the viruses may include herpes Simplex, herpes Zoster, and adenovirus; the proteins may include lactorferrin, Tryptase, and interleukins; and the small molecules may include histamine, glucose, and fructose.

A disposable sensor for analyte detection via surface plasmon resonance comprises, in accordance with the present invention, a body having a predetermined geometric configuration for attachment to an analyte detection device that includes light beam generation componentry, light beam transmission or guidance components, a photodetector, and a computing unit. The disposable sensor also comprises a substrate of a noble metal provided on a sensing surface of the body, and a plurality of different binding agents adhered to the substrate on the sensing surface. The different binding agents are disposed in respective locations on the substrate, mutually spaced from each other along the sensing surface. The different binding agents are preselected to couple with respective solutes or analytes.

When needed, a multiplicity of molecular agents are attached at least indirectly to the sensing surface to enhance wettability thereof, so that a liquid placed into contact with the sensing surface spreads over the sensing surface to achieve contact therewith including at preselected locations or regions on the substrate.

Preferably the molecular agents for enhancing surface wettability collectively comprise a surface-assembled monolayer. The surface-assembled monolayer may be configured to alter a contact angle of solvent or water droplets on the sensor surface. The surface-assembled monolayer may be configured to confer a variable proportion of hydrophilicity and hydrophobicity to the sensing surface. In other words, different SAM elements may be deposited and attached to the sensor surface at different locations or regions, depending on the functionalities (the target solutes or analytes), the binding agents, and the type of liquid sample (hydrophobic or hydrophilic).

It is contemplated that the substrate of the noble metal is a film with a thickness between 15 and 100 nm and that the noble metal is Au, Ag, Al, Pt, Rh, Cu, or Ni or possibly mixtures or alloys thereof. In addition, the sensing surface may include an adhesive layer between 0.01 and 50 nm thick attaching the metal layer, film, or coating to the body of the disposable sensor. The noble metal film may have a hydrophilicity or hydrophobicity altered via an a plasma process. Typically a plasma process is used only if necessary and at the end of manufacture or preparation of the sensing surface.

A method of measuring concentration of at least one analyte of a fluid sample comprises, in accordance with the present invention, measuring a position or positions of one or more SPR minima and correlating the positions of the SPR minima with positions of SPR minima of known control samples or known indexes of refraction, to determine at least one unknown sample composition or at least one unknown analyte concentration. Alternatively or additionally, the method may include using one or more SPR minima measurements to correct other SPR minima in the same measurement for environmental factors, for instance air humidity, temperature, and/or barometric pressure. Alternatively or additionally, the method may include a step of using one or more SPR minima measurements to correct other SPR minima in the same measurement for manufacturing deviations or errors, including noble metal thickness, adhesion layer thickness and the molded sensor prism refractive index.

A second-generation method and apparatus pursuant to the present invention reduces testing time, expediting medical diagnoses and treatment. In addition, costs may be reduced for many purposes.

A method for manufacturing a sensor for analyte detection via surface plasmon resonance comprises, in accordance with the present invention, providing a body having a surface formed with a noble metal coating or film, operating a pico- or nano-dot printer to deposit a plurality of solute- or analyte-binding agents in different mutually spaced regions or locations on the noble metal coating or film, and attaching the solute- or analyte-binding agents to the noble metal coating or film at the different mutually spaced regions or locations. The solute- or analyte-binding agents are configured for coupling with respective constituents of a liquid sample deposited on the sensing surface.

The manufacturing method may further comprise operating the pico- or nano-dot printer or another pico- or nano-dot printer to deposit or print a plurality of surface-assembled monolayer elements on the surface of the body and particularly on the noble metal coating or film.

The depositing of the plurality of solute- or analyte-binding agents in different regions or locations on the noble metal coating or film may be performed after the depositing of the plurality of surface-assembled monolayer elements on the sensing surface. In that event, the attaching of the solute- or analyte-binding agents to the noble metal coating or film at the different mutually spaced regions or locations comprises attaching the solute- or analyte-binding agents to the noble metal coating or film via the surface-assembled monolayer elements.

The manufacturing method optionally comprises selecting an additional plurality of surface-assembled monolayer elements to control wettability of the noble metal coating or film and printing the additional plurality of surface-assembled monolayer elements on the noble metal coating or film, preferably after the printing or depositing of the solute- or analyte-binding agents.

DETAILED DESCRIPTION

Figure 1A:
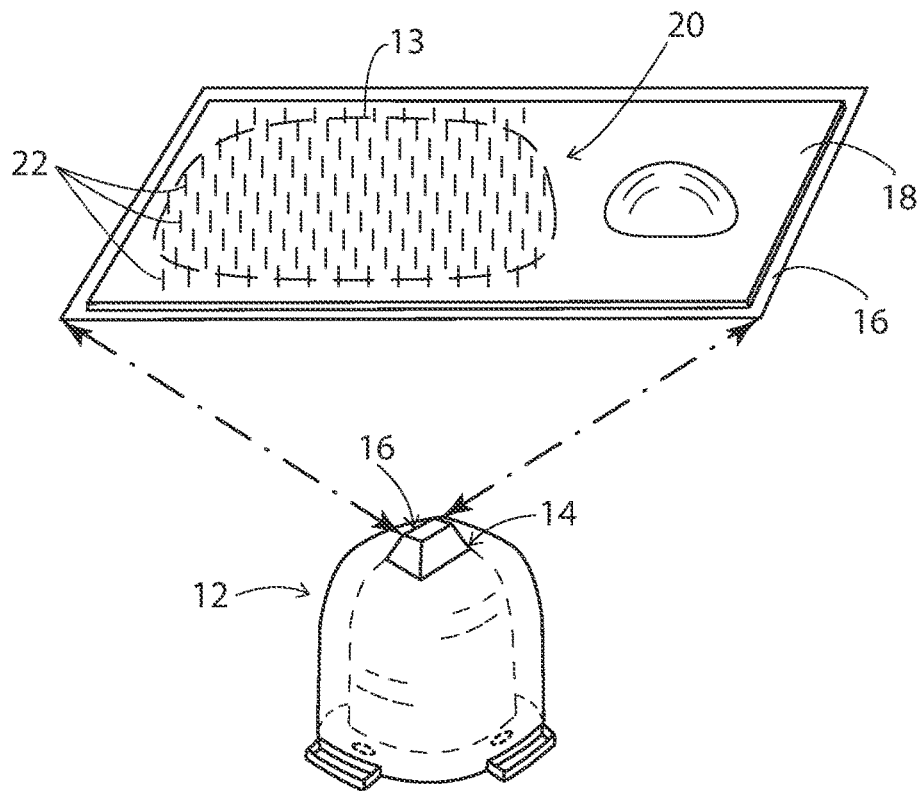
FIG. 1A is partly a perspective view of a disposable sensor component and a schematic elevational view on a larger scale of a sensing surface or film included in the sensor component, in accordance with the present invention.
Figure 1B:
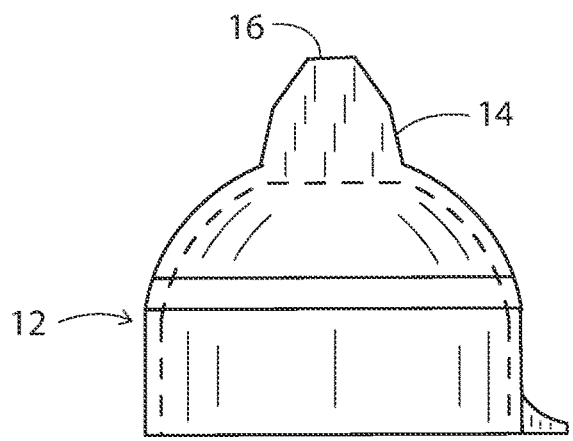
FIG. 1B is a schematic side elevational view of the sensor component illustrated in FIG. 1A.
Figure 1C:
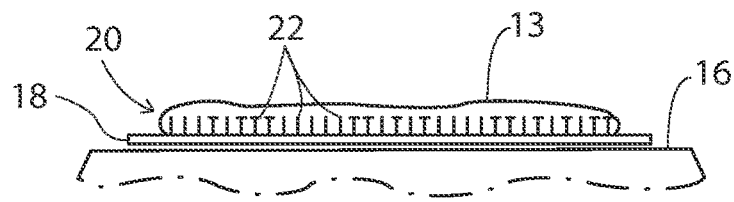
FIG. 1C is a schematic side or edge elevational view of a distal end of the sensor component of FIGS. 1A and 1B, on an enlarged scale.

FIGS. 1A-1C show a disposable sensor 12 that is attachable to an applicator end of a hand-held SPR device such as that disclosed in U.S. Pat. No. 8,249,682, incorporated herein by reference. Sensor 12 includes a sensor body or prism 14 having a sensing surface 16 at one end that may be brought into contact with a target liquid. Sensing surface 16 carries substrate 18 in the form of a film, layer, or coating with a thickness between 15 and 100 nm and made of a noble metal such as Au, Ag, Al, Pt, Rh, Cu, and Ni. The hand-held SPR device (see FIG. 7 et seq.) cooperates with sensor 12 to detect the presence in a liquid aliquot of any of a preselected group of potential analytes or solutes and to measure the concentrations of the detected analytes or solutes.

As depicted in FIGS. 1A and 1C, sensing surface 16 and particularly film, layer or coating 18 is provided with a surface-assembled monolayer (SAM) 20 comprising a multiplicity of molecular agents 22 attached to substrate, film, coating, or layer 18 and thus indirectly to sensing surface 16 to control or adjust the degree of wettability of the noble-metal substrate 18. In many cases, it is desirable to enhance the wettability of the sensing surface 16, so that a liquid sample 13 placed on sensing surface 16 spreads over at least a portion of the sensing surface to achieve contact with one or more active areas or locations 24, 26, 28 (see FIG. 5) thereof. FIG. 1A shows an aqueous droplet 13' that does not spread out but rather beads up on a gold or noble metal substrate 18 that is not provided with a wettability-enhancing SAM of otherwise treated, for instance, via an oxygen plasma.

Figure 5:
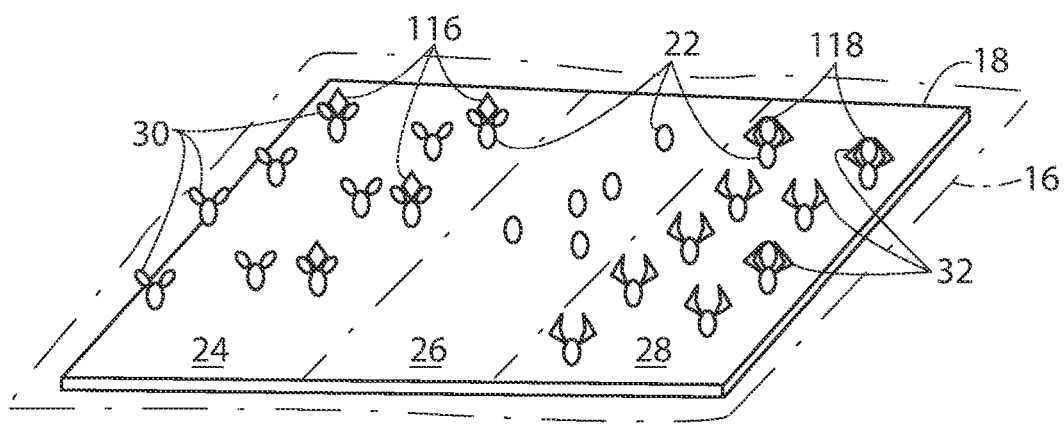
FIG. 5 is a diagram depicting generation of three SPR curves from 3 unique positions on the noble metal sensor surface of the sensor prism of FIG. 1.

As depicted in FIG. 5, one or more of the active areas or locations 24, 26, 28 are functionalized by respective solute- or analyte-binding agents 30, 32 adhered to substrate 18 on sensing surface 16 in or on the different active areas. Active areas or locations 24, 26, 28 and concomitantly their respective binding agents 30 32 are mutually spaced from each other along sensing surface 16 and are preselected to couple with respective predetermined solutes or analytes.

Surface-assembled monolayer 20 may include alkane thiol groups attached to the metal film, layer or coating of substrate 18. The alkane thiol groups may function in part to attach antibodies and other preselected solute- or analyte-binding agents to noble-metal substrate or film 18. At least some of the alkane thiol groups may be each provided with a terminal hydrophobic head. The terminal hydrophobic head may be an acidic hydrophobic head, a hydroxyl hydrophobic head, or an amino group. The terminal hydrophobic head may be $SH—(CH_2)_n—COOH$ or $SH—(CH_2)_n$.

Surface-assembled monolayer 20 may include both hydrophilic and hydrophobic elements in preselected amounts to vary the hydrophilicity/hydrophobicity of the predetermined regions. The wettabilty (hydrophilicity/hydrophobicity) of sensing surface 16 and more particularly noble metal substrate or film 18 is adjusted or controlled to promote capture or target solutes or analytes in the respective locations or regions 24, 26, 28, depending on the carrier or the liquid sample (e.g., oily or aqueous), the solute- or analyte-binding agents 30, 32 (e.g., antibodies), and the target solutes or analytes (e.g., antigens), as well as on the SAM elements 22 or other coupling agents that anchor the solute- or analyte-binding agents 30, 32 to the metal substrate or film 18.

Additional SAMs may be beaded to the surface-assembled monolayer 20 and configured to alter a contact angle of solvent or water droplets on sensing surface 16. Monolayer 20 may be assembled so as to confer a variable proportion of hydrophilicity and hydrophobicity to sensing surface 16.

Figure 2:
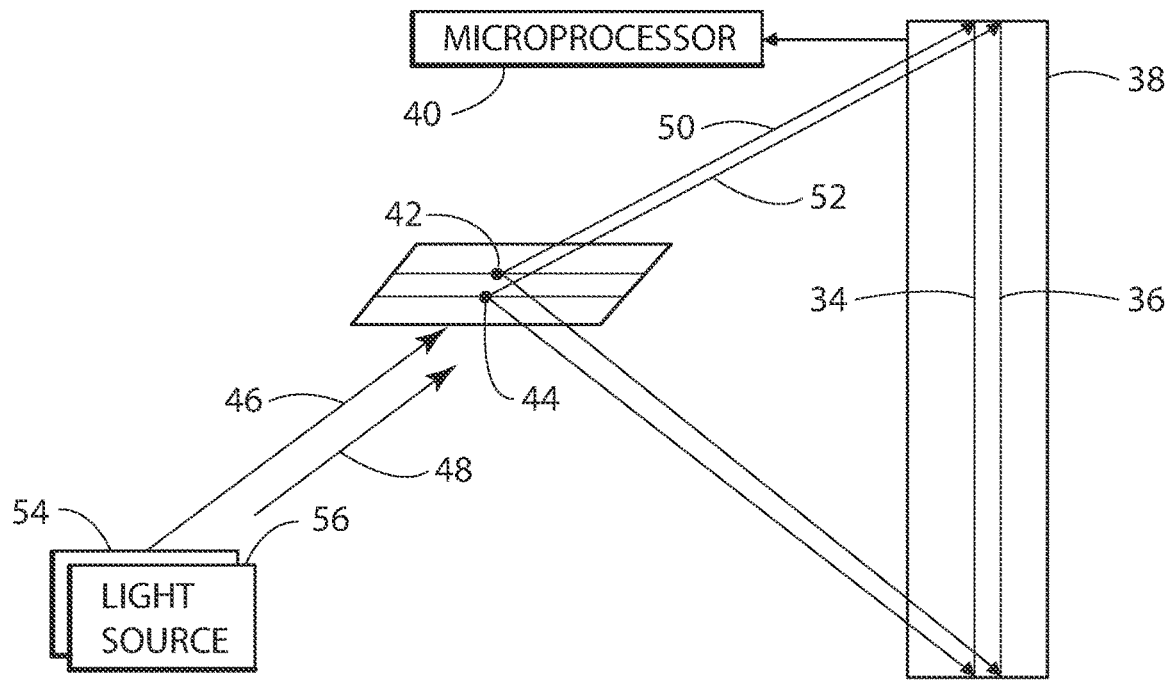
FIG. 2 is a diagram depicting generation of two SPR curves from two excitation spots or active areas on a noble metal surface of the sensor component of FIG. 1.

FIG. 2 depicts incidence of reflected light energy along two lines 34, 36 of photoelements in a linear array 38, for generation by a microprocessor 40 of respective SPR curves (see FIG. 6) from two mutually spaced excitation spots or active areas 42, 44 on noble metal substrate or film 18 of sensing surface 16. Two illumination or incident beams 46, 48 are directed to the underside of noble-metal substrate or film 18, through prism 12, and transmit as reflected beams 50, 52 to lines 34, 36 of photoelements or pixels in linear array 38. Illumination beams 46, 48 emanate from respective light sources 54, 56 and may have the same wavelength or different wavelengths.

Figure 3:
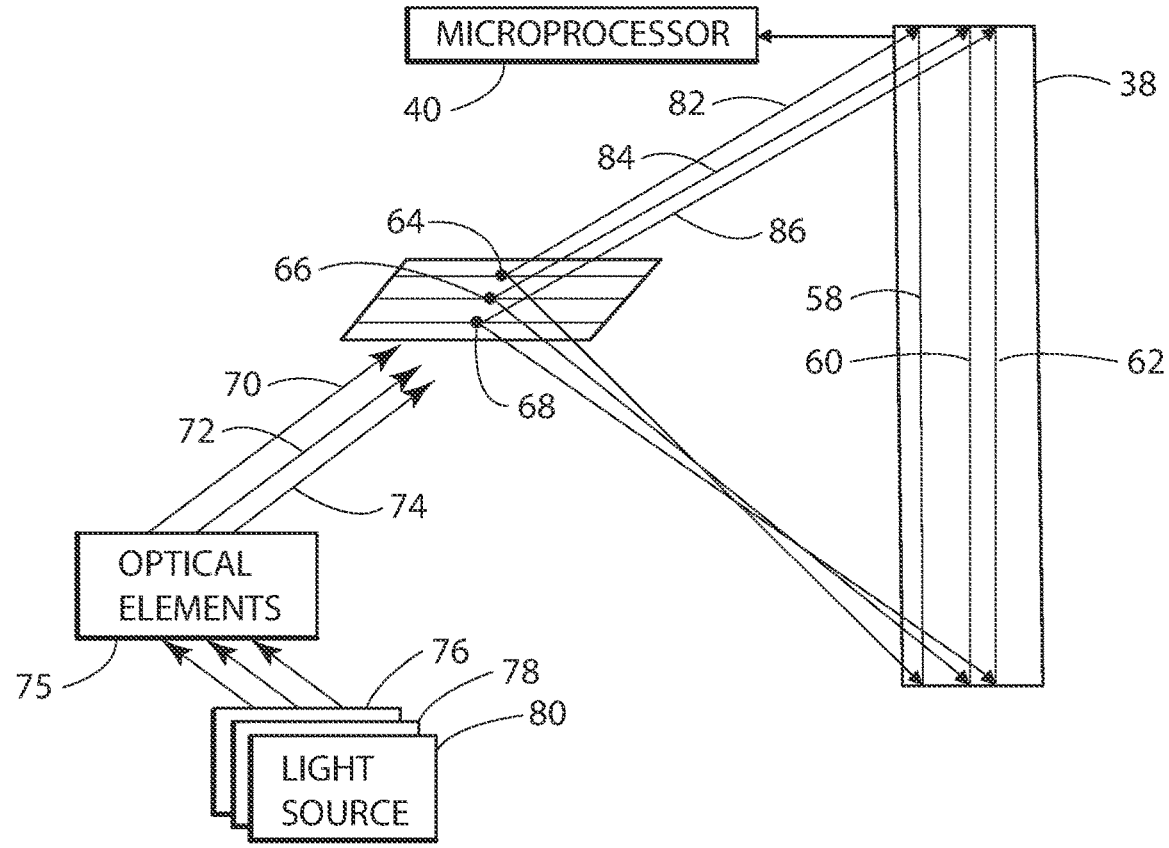
FIG. 3 is a diagram depicting generation of three SPR curves from three excitation spots on a noble metal surface of the sensor component of FIG. 1.
Figure 4:
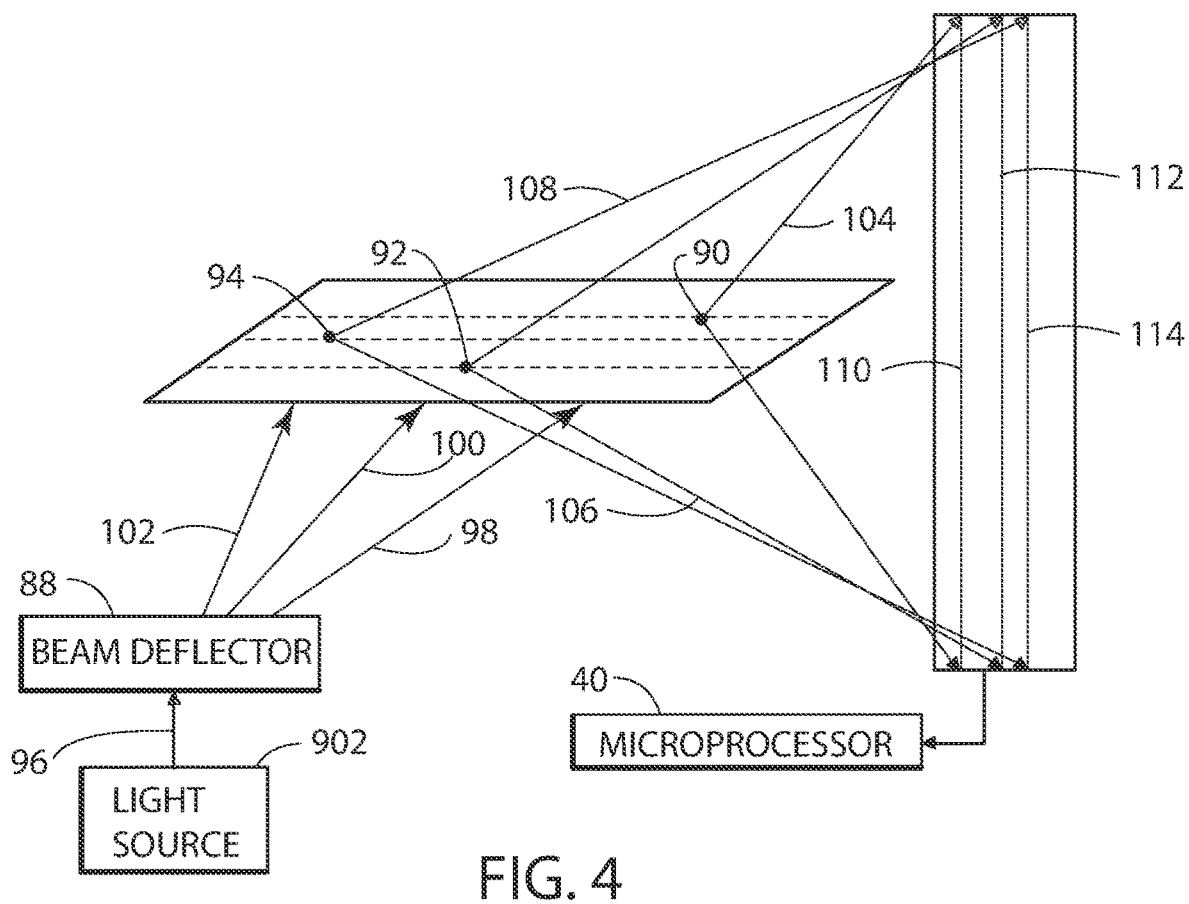
FIG. 4 is a diagram depicting generation of three SPR curves from one sole excitation (light) source.

FIG. 3 shows incidence of reflected light energy along three lines 58, 60, 62 of photoelements in linear array 38, for generation by microprocessor 40 of respective SPR curves (see FIG. 6) from three mutually spaced excitation spots or active areas 64, 66, 68 on noble metal substrate or film 18 of sensing surface 16. Three illumination or incident beams 70, 72, 74 are directed via appropriate optics 75 from respective sources 76, 78, 80 to impinge at varying angles (to detect SPR minima) on the underside of noble-metal substrate or film 18, through prism 12. Reflected beams 82, 84, 86 of varying angular directionality fall on photo-element lines 58, 60, 62 in array 38. (The illustrations of FIGS. 2-4 are schematic in that the reflected beams, for instance beams 82, 84, 86, will pass back through prism 14 and be directed by optical elements to fall on the light-sensitive opto-electrical elements of linear array 38 or CCD.) The light of beams 70, 72, 74 may have the same wavelength or different wavelengths.

As depicted in FIG. 4, an SPR sensing device as disclosed in U.S. Pat. No. 8,249,682 may be modified to include mechanical or electro-mechanical beam deflectors 88 and pertinent optics to focus light from a single light source 902 in seriatim at different locations 90, 92, 94 and with a varying impingement angle along an underside of metal film, coating or layer 18. FIG. 4 shows a single beam 96 directed by beam deflectors and optics 88 along three spaced paths 98, 100, 102 to locations 90, 92, 94. From those spaced locations or regions, functionalized for binding with respective solutes or analytes as discussed above, respective reflected beams 104, 106, 108 of varying reflection angles travel to illuminate linear array 38 along three lines 110, 112, 114. Microprocessor 40 processes the outputs of the photoelectric elements of the linear array 38 to generate three SPR curves. This approach provides the advantage that all 3 SPR curves are generated essentially simultaneously and not sequentially and via a single sensor prism and its sensing surface. In either case, the present invention contemplates an effectively simultaneous processing of a single liquid sample 13 (FIG. 1A) to enable identification of multiple solutes or analytes in the sample, as well as measurement of the concentrations of those solutes or analytes.

As illustrated in FIG. 5, three SPR curves may be generated effectively simultaneously by directing light to three predetermined mutually spaced positions or active areas or regions 24, 26, 28 on noble metal substrate 18 of the sensor prism 12. On an upper or outer side of substrate 18, areas 24 and 28 spaced from one another are provided with respective binding agents 30, 32 particularly respective antibodies for binding respective antigens 116, 118. Third area 26, between areas 24 and 28 may be bare metal of a gold substrate or layer 18 for osmolarity or reference measurement as described in U.S. Pat. No. 8,249,682. Thus two spatial positions or locations 24 and 28, with respective analyte-coupling functionalities, result in detection of two unique analytes (e.g., antigens) and measurement of their concentrations.

Figure 6:
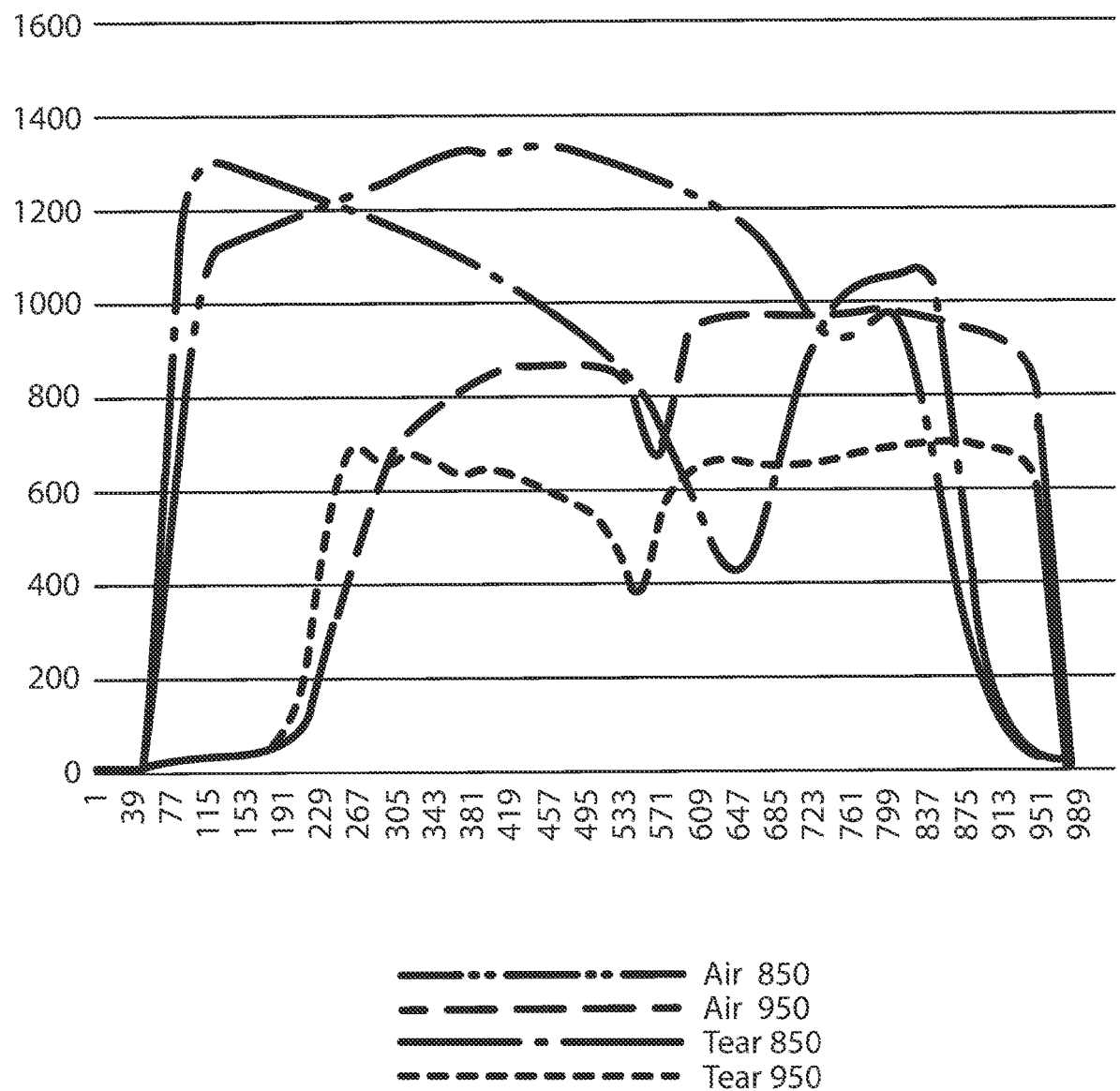
FIG. 6 is a graph showing SPR data, particularly a two-plex measurement of both air and a tear solution, measured at 2 unique wavelengths, 855 and 950 nm respectively, where the Y-axis is intensity and the X-axis is pixel position on a linear array.

FIG. 6 shows SPR measurement data measured as described above, showing a two-plex measurement of both air and a tear solution, measured at two unique wavelengths, 855 and 950 nm respectively. The air position was different than the position where the tear solution was measured on the gold SPR film.

After the deposition of noble metal substrate or film 18 on sensing surface 16 of sensor prism 14, typically over an adhesion layer exemplarily of chromium in the case of a gold substrate or film 18, one uses a micro-dot printer or plotter (e.g., Nano-Plotter™ of GeSim, https://gesim-bioinstruments-microfluidics.com/microarray-printer/) to deposit the molecular agents or components 22 of surface-assembled monolayer 20 on noble metal substrate or film 18. Different molecular agents 22, and concomitantly different SAMs, may be deposited or printed at different locations or regions 24, 28 depending in part on the nature of the solute- or analyte-binding agents 30, 32. Should the molecular agents or components 22 have insufficient functionality in generating appropriate surface wettability, the gold or other noble metal film 18 may be further provided with additional SAMs as required for creating a desirable degree or wettability in the different active areas or regions 24, 28 of the sensing surface 16.

Typically, a manufacturing process includes a first printing of SAM elements 22 of possibly different types respectively in the different active areas or regions 24, 28 of sensing surface 16. In a subsequent, second, printing step, solute- or analyte-binding agents 30, 32 are deposited in the respective active areas or regions 24, 28 of sensing surface 16 to bind to the active ends of the respective SAM elements 22. In a third printing step, different SAMs 22 may be deposited or printed onto sensing surface 16 and particularly substrate or film 18, to adjust the hydrophilicity/hydrophobicity of noble metal substrate or film 18 in the active areas or regions 24, 28. Finally, if necessary, sensing surface, that is, substrate or film 18, may be exposed to a plasma such as of $O_2$ gas to enhance wettability of the substrate or film.

Typically, molecular agents or components 22 of respective surface-assembled monolayers 20 serve to attach solute- or analyte-binding agents 30, 32 to metal substrate or film 18 at respective regions or areas 24, 28. To that one, manufacturing includes using the same or a different micro-dot printer or plotter to deposit the solute- or analyte-binding agents (e.g., antibodies 30, 32) at the respective predetermined active areas 24, 28 (FIG. 5) on substrate or film 18. The solute- or analyte-binding agents may be deposited in any shape or configuration, such as linear, circular, or rectangular, optionally of different sizes. In addition, the solute- or analyte-binding agents may be deposited or printed in different densities or strengths, for instance, at different positions, whether in the same active area or different active areas of substrate or film 18. The differentiation in SPR strength or sensitivity facilitates collection of more information, for instance, as to solute concentrations.

The printer or plotter used to prepare sensing surface 16 enables precise deposition, both as to location as well as thickness of the microscopic layer, of various layers on the sensing surface, including wetting-control SAM layers 20, and ligands (e.g., 30, 32) necessary for functionalization of the SPR surface (substrate or film 18). Such a printer or plotter utilizes a Jetting-based bio-printing technology, entailing a non-contact technique whereby 2D structures are built using picolitre bio-ink droplets layered onto a substrate. The jetting-based bio-printing methods can eject droplets of picolitre volume with high spatial resolution. (In general, the term "micro" used above pertains to a linear dimension, whereas "pico" pertains to a volumetric dimension. Some bio-printer makers use the intermediate term "nano" that ostensibly references the area of a dot or droplet as deposited.)

As described above, a multiplexing analyte-sensing apparatus using surface plasmon resonance (SPR) has a sensing surface 16 with a noble-metal film or coating 18 differentially and spatially functionalized (e.g., via binding agents 30, 32) for interacting with a plurality of different solutes or analytes in a liquid sample placed into contact with the sensing surface. As additionally described above, the apparatus includes, a light-sensing device 38 such as a linear array or CCD camera, and a computer or microprocessor 40 operatively linked to the light-sensing device for receiving therefrom an electrical signal or a plurality of electrical signals encoding patterns of light absorption by the sensing surface. Computer or microprocessor 40 is programmed to analyze data from light-sensing device 38 to ascertain concentrations of different solutes in a single contiguous or unitary sample 13 in contact with sensing surface 13 and particularly substrate or film 18 by analyzing the patterns of light intensity as a function of angle of reflection. To differentially functionalize sensing surface 16, substrate or film 18 is provided with a plurality of different molecular elements or ligands 30, 32 configured to bind with respective solutes or analytes, the different molecular elements or ligands being disposed on the sensing surface at respective predetermined regions spaced from each other. Thus, sensing surface 16 is spatially coded and functionally divided or compartmentalized for detecting the presence of respective solutes or analytes and their associated concentrations. The SPR apparatus further comprises at least one light source 54, 56, 76, 78, 80, 90 and optical transmission elements disposed at least in part between the light source and sensing surface 16 and configured for directing respective beams of electromagnetic radiation 46, 48, 70, 72, 74, 96 toward respective predetermined regions or active areas 24, 26, 28, 42, 44, 64, 66, 68 and on an underside of sensing surface 16, opposite the liquid sample 13, so that reflected beams 50, 52, 82, 84, 86, 104, 106, 108 from the underside of sensing surface 16 impinge on light sensing device 38. Optical transmission elements (not shown) may be disposed in part also between solute sensing surface 16 and light sensing device 38.

As described hereinabove, surface-assembled monolayer 20 may include alkane thiol groups 22 attached to metal substrate or film 18. It is a principal function of alkane thiol groups 22 to attach and bind antibodies to substrate or film 18 of sensing surface 16. However, alkane thiol groups 22 have an additional important functionality, in modifying, for instance, enhancing, the wettability of the sensing surface 16. If the particular alkane thiol type groups or other coupling agents 22 used for functionalizing sensing surface 16 do not exhibit a desired degree of wettability, additional SAM groups may be deposited on sensing surface 16 and particularly on substrate or film 18. These additional SAM groups, like the functionalizing SAMs with their respective solute- or analyte-binding agents 30, 32, may be of different types and deposited in different active areas 24, 28 to achieve different degrees of hydrophilicity/hydrophobicity. Alternatively, or additionally, sensing surface and metal substrate or film 18 may be exposed to a plasma such as O2 gas. This exposure occurs only at the end of the manufacturing process, after the printing of the various functional groups and agents.

At least some of the alkane thiol groups 22 may be each provided with a terminal hydrophobic head taken from the group consisting of acidic hydrophobic heads, hydroxyl hydrophobic heads, or amino groups. The terminal hydrophobic head may be $SH-(CH_2)_n-COOH$ or $SH-(CH_2)_n$. As discussed above, surface-assembled monolayers 20 provided on metal substrate or film 18 may include hydrophilic and hydrophobic elements in preselected amounts to vary the hydrophilicity/hydrophobicity of the surface-assembled monolayer over the predetermined regions.

Computer or microprocessor 40 is configured to detect multiple analytes in liquid sample 13 effectively simultaneously. An electrical signal from light sensing device 38 includes signals of different opto-electrical elements or pixels in a predetermined sequence whereby the computer or microprocessor monitors SPR light signals from different regions or active areas 24, 26, 28, 42, 44, 64, 66, 68 of sensing surface 16 substantially in real time and in interleaved simultaneity.

Liquid sample 13 exemplarily consists of biological fluid, human fluid, animal fluid, food, or beverages. The solutes or analytes, the presence and/or concentrations of which are detected, may be cells, bacteria, insect constituents, vegetable constituents, viruses either directly or their respective lysates, proteins, DNA and RNA, dissolved cations or anions, endosomes, enzymes, lipids, pharmaceutical compounds, natural and artificial drugs, small molecules, or dissolved gasses. The enzymes may include mmp-9; the viruses may include herpes Simplex, herpes Zoster, and adenovirus; the proteins may include lactorferrin, Tryptase, and interleukins; and the small molecules may include histamine, glucose, and fructose.

It is contemplated that noble metal substrate or coating has a thickness between 15 and 100 nm and that the noble metal is Au, Ag, Al, Pt, Rh, Cu, or Ni or possibly mixtures or alloys thereof. In addition, sensing surface 16 optimally includes an adhesive layer, e.g., of chromium, between 0.01 and 50 nm thick for attaching the metal layer, film, or coating 18 to prism or body 14 of disposable sensor 12. Noble metal substrate or film 18 may have a hydrophilicity or hydrophobicity altered via an a plasma process.

In a method of measuring concentration of at least one solute, dissolved constituent, or analyte of a fluid sample, one measures a position or positions of one or more SPR minima and correlates the positions of the SPR minima with positions of SPR minima of known control samples or known indexes of refraction, to determine at least one unknown sample composition or at least one unknown analyte concentration. Alternatively or additionally, one uses one or more SPR minima measurements to correct other SPR minima in the same measurement for environmental factors, for instance air humidity, temperature, and/or barometric pressure. Alternatively or additionally, the method may include a step of using one or more SPR minima measurements to correct other SPR minima in the same measurement for manufacturing deviations or errors, including noble metal thickness, adhesion layer thickness and the molded sensor prism refractive index.

Clinical uses of the present invention include in ophthalmologic diagnosis of pink eye and dry eye. 50% of cornea specialists can not distinguish between viral, bacterial or allergic etiology. The present sensing apparatus facilitates such determinations. The present invention contemplates a disposable sensor attachment or cap 12 with three different biofilm ribbons or functionalized areas 24, 26, 28 (FIG. 5) on sensing substrate 18, with light beams 70, 72, 74 (FIG. 3) or 98, 102, 104 (FIG. 4) from sources 76, 78, 80 or 90, respectively, focused on each ribbon or location 82, 84, 86 or 90, 92, 94. One tear sample, deposited on sensing substrate 18 with one touch of the substrate to a tear, typically in vivo, will elicit three essentially or practically simultaneous SPR signals and three different diagnosis, all in one second.

For dry eye, sensing substrate or film 18 preferably comprises plain or substantially pure gold on one-half of sensing substrate 18 with MMP-9 antibody loaded via a SAM 20 on the other half. Two diagnoses may be accomplished in one test.

In urologic applications, a sensor 12 and associated sensing apparatus as described herein may be used to detect and quantitatively assess urinary tract infections. Sensor surface 16, or more particularly, sensing substrate or film 18, is printed with an antibody film containing *E. Coli, Klebsiella* and *Enterococcus*, which covers 90+% of bacteria causing such infections. In addition, urethral discharge may be simultaneously tested for G.C., *Chlamydia* and Syphilis.

In veterinary medicine, the present invention enables simultaneous measurement of osmolarity and MMP-9, for dry eye diagnoses. UTIs are more common in cats.

In the meat and vegetable industries, the present invention enables simultaneous detection of multiple contaminants and a quantitative measurement of their presence in a tested sample.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A spatially multiplexed analyte sensing apparatus using surface plasmon resonance, said apparatus comprising:
   a hand-holdable housing or hand-holdable casing;
   a sensor attached to said hand-holdable housing or hand-holdable casing and having a sensing surface located in a plane on an outer side of said hand-holdable housing or hand-holdable casing at an end thereof, whereby said sensing surface is disposed for contacting a surface of a liquid sample, said sensing surface being configured to interact with each of a plurality of different types of solutes in the liquid sample;
   a light-sensing device disposed inside said hand-holdable housing or hand-holdable casing;
   a computer or microprocessor disposed inside said hand-holdable housing or hand-holdable casing and operatively linked to said light-sensing device for receiving therefrom a plurality of electrical signals encoding patterns of light absorption by said sensing surface, said computer or microprocessor being programmed to analyze data from said light-sensing device to determine presence of the different types of solutes in said liquid sample in contact with said sensing surface,
   wherein said sensing surface is provided with a plurality of different molecular elements or ligands configured to bind with respective ones of said different types of solutes, said plurality of different molecular elements or ligands being attached to said sensing surface and facing outwardly away from said hand-holdable housing or hand-holdable casing for direct contact with said liquid sample, said different molecular elements or ligands being disposed in said plane within respective predetermined regions that are separate and distinct from each other;
   a plurality of light sources disposed inside said hand-holdable housing or hand-holdable casing and emitting respective beams of electromagnetic radiation with respective wavelengths different from one another;
   transmission elements disposed inside said hand-holdable housing or hand-holdable casing at least in part between said plurality of light sources and said sensing surface and configured for directing said respective beams of electromagnetic radiation at least approximately simultaneously toward respective ones of said predetermined regions and on an underside of said sensing surface, opposite the liquid sample, with reflected beams from the underside of said sensing surface impinging substantially simultaneously on said light sensing device,
   wherein said computer or microprocessor is configured to detect presence of said different types of solutes in said liquid sample substantially simultaneously in response to the reflected beams from the underside of the sensing surface impinging on the light sensing device.

2. The apparatus of claim 1 wherein said sensing surface includes at least one metal film, layer or coating, said predetermined regions being on said at least one metal film, layer or coating.

3. The apparatus of claim 2 further comprising a liquid-transport vehicle in the form of at least one surface-assembled monolayer provided on said sensing surface, said at least one surface-assembled monolayer serving at least in part to enhance spreading of said liquid sample over said sensing surface so that said liquid sample moves into effective contact with said at least one metal film, layer or coating at each of said predetermined regions.

4. The apparatus of claim 3 wherein said surface-assembled monolayer includes alkane thiol groups attached to said at least one metal film, layer or coating.

5. The apparatus of claim 4 wherein said alkane thiol groups are each provided with a terminal hydrophobic head taken from the group consisting of acidic hydrophobic heads, hydroxyl hydrophobic heads, or amino groups.

6. The apparatus of claim 3 wherein said surface-assembled monolayer includes both hydrophilic and hydrophobic elements in preselected amounts to vary the hydrophilicity/hydrophobicity of said surface-assembled monolayer over said predetermined regions.

7. The apparatus of claim 3 wherein said surface-assembled monolayer includes elements taken from the group consisting of:
   a. an alkane thiol group attached to said at least one metal film, layer or coating, said alkane thiol group provided with a terminal hydrophobic head SH—$(CH_2)_n$—COOH;
   b. an alkane thiol group attached to said at least one metal film, layer or coating, said alkane thiol group provided with a terminal hydrophobic head SH—$(CH_2)_n$; and
   c. a mixture of both hydrophilic and hydrophobic surface-assembled monolayer elements to tune the hydrophilicity/hydrophobicity of the at least one metal film, layer or coating.

8. The apparatus of claim 1 wherein said liquid sample is taken from the group consisting of biological fluid, human fluid, animal fluid, food, and beverages, and wherein said solutes are taken from the group consisting of cells, bacteria, insect constituents, vegetable constituents, viruses either directly or their respective lysates, proteins, DNA and RNA, dissolved cations or anions, endosomes, enzymes, lipids, pharmaceutical compounds, natural and artificial drugs, small molecules, dissolved gases.

9. The apparatus as set forth in claim 8 wherein the enzymes include mmp-9; the viruses include herpes Simplex, herpes Zoster, and adenovirus; the proteins include lactorferrin, Tryptase, and interleukins; and the small molecules include histamine, glucose, and fructose.

10. The apparatus of claim 1 wherein:
said sensor is disposable,
said light-sensing device, said computer or microprocessor, said plurality of light sources and said transmission elements are mounted to said hand-holdable housing or hand-holdable casing,
said sensor comprises a body having a predetermined geometric configuration for removable attachment to said hand-holdable housing or hand-holdable casing, said sensing surface including a substrate of a noble metal disposed on said body.

11. The apparatus of claim 10 wherein said substrate is treated to control or adjust wettability thereof.

12. The apparatus of claim 11 wherein the treatment of said substrate to control or adjust wettability thereof includes a multiplicity of molecular agents attached at least indirectly to said sensing surface, the multiplicity of molecular agents comprising a surface-assembled monolayer.

13. The apparatus of claim 12 wherein said surface-assembled monolayer is configured to alter a contact angle of solvent or water droplets on said sensing surface.

14. The apparatus of claim 12 wherein said surface-assembled monolayer is configured to confer a variable proportion of hydrophilicity and hydrophobicity to said sensing surface.

15. The apparatus of claim 10 wherein:
said substrate of said noble metal is a film with a thickness between 15 and 100 nm;
said noble metal is taken from the group consisting of Au, Ag, Al, Pt, Rh, Cu, and Ni; and
said sensing surface includes an undercoat of an adhesive layer between 0.01 and 50 nm thick.

16. The apparatus of claim 10 wherein said substrate of said noble metal is a metal film with a hydrophilicity or hydrophobicity altered via a plasma process.

17. The apparatus of claim 4 wherein said terminal hydrophobic head is taken from the group consisting of SH—$(CH_2)_n$—COOH and SH—$(CH_2)_n$.

18. The apparatus of claim 4 wherein said plurality of molecular elements or ligands are attached to active ends of said alkane thiol groups, opposite said at least one metal film, layer or coating.

19. A spatially multiplexed analyte sensing apparatus using surface plasmon resonance, said apparatus comprising:
a hand-holdable housing or hand-holdable casing;
a sensor attached to said hand-holdable housing or hand-holdable casing and having a sensing surface located in a plane on an outer side of said hand-holdable housing or hand-holdable casing at an end thereof, whereby said sensing surface is disposed for contacting a liquid tear sample in situ on a person's eye and configured to interact with each of a plurality of different types of solutes in the liquid tear sample;
a light-sensing device disposed inside said hand-holdable housing or hand-holdable casing;
a computer or microprocessor disposed inside said hand-holdable housing or hand-holdable casing and operatively linked to said light-sensing device for receiving therefrom a plurality of electrical signals encoding patterns of light absorption by said sensing surface, said computer or microprocessor being programmed to analyze data from said light-sensing device to determine presence of the different types of solutes in the liquid tear sample in contact with said sensing surface,
wherein said sensing surface comprises a plurality of sensing regions separate and distinct from one another and configured for detection of respective types of solutes in said liquid tear sample, one of said sensing regions being configured for detection of salt ions and at least one other of said sensing regions being provided with molecular elements or ligands configured to bind with a type of solute different from salt ions, said molecular elements or ligands being disposed on said sensing surface only within said at least one other of said sensing regions;
at least one light source disposed inside said hand-holdable housing or hand-holdable casing;
transmission elements disposed inside said hand-holdable housing or hand-holdable casing at least in part between said at least one light source and said sensing surface and configured for directing respective beams of electromagnetic radiation at least approximately simultaneously toward respective ones of said sensing regions and on an underside of said sensing surface, opposite the liquid tear sample, with reflected beams from the underside of said sensing surface impinging substantially simultaneously on said light sensing device, wherein said computer or microprocessor is configured to detect presence of at least salt ions and said type of solute in said liquid tear sample effectively substantially simultaneously in response to the reflected beams from the underside of the sensing surface impinging on the light sensing device.

20. A spatially multiplexed analyte sensing apparatus using surface plasmon resonance, said apparatus comprising:

- a hand-holdable housing or hand-holdable casing;
- a sensor attached to said hand-holdable housing or hand-holdable casing and having a sensing surface located in a plane on an outer side of said hand-holdable housing or hand-holdable casing at an end thereof, whereby said sensing surface is disposed for contacting a surface of a liquid sample, said sensing surface being configured to interact with each of a plurality of different types of solutes in the liquid sample;
- a light-sensing device disposed inside said hand-holdable housing or hand-holdable casing;
- a computer or microprocessor disposed inside said hand-holdable housing or hand-holdable casing and operatively linked to said light-sensing device for receiving therefrom a plurality of electrical signals encoding patterns of light absorption by said sensing surface, said computer or microprocessor being programmed to analyze data from said light-sensing device to determine presence of the different types of solutes in liquid sample in contact with said sensing surface,
- wherein said sensing surface is provided with a plurality of different molecular elements or ligands configured to bind with respective ones of said different types of solutes, said plurality of different molecular elements or ligands being attached to said sensing surface and facing outwardly away from said hand-holdable housing or hand-holdable casing for direct contact with said liquid sample, said different molecular elements or ligands being disposed in said plane only within respective predetermined regions that are separate and distinct from each other;
- at least one light source disposed inside said hand-holdable housing or hand-holdable casing;
- transmission elements disposed inside said hand-holdable housing or hand-holdable casing at least in part between said at least one light source and said sensing surface and configured for directing respective beams of electromagnetic radiation at least approximately simultaneously toward respective ones of said predetermined regions and on an underside of said sensing surface, opposite the liquid sample, with reflected beams from the underside of said sensing surface impinging substantially simultaneously on said light sensing device,
- wherein said computer or microprocessor is configured to detect presence of said different types of solutes in said liquid sample substantially simultaneously in response to the reflected beams from the underside of the sensing surface impinging on the light sensing device.

* * * * *